United States Patent [19]

Ritter

[11] 4,259,955

[45] Apr. 7, 1981

[54] APPLICATOR SWAB AND METHOD OF MAKING THE SAME

[76] Inventor: Barbara Ritter, 235 E. 87 St., New York, N.Y. 10028

[21] Appl. No.: 929,324

[22] Filed: Jul. 31, 1978

[51] Int. Cl.³ .................................................. A61M 35/00
[52] U.S. Cl. .................................. 128/269; 15/210 R
[58] Field of Search .............. 128/269, 260, 638, 759, 128/743, 263, 267, 756; 15/210 R, 209 R, 209 D, 229 AC, 229 BC, 229 BP; 401/12, 268

[56] References Cited

U.S. PATENT DOCUMENTS

| | | | |
|---|---|---|---|
| 1,517,864 | 12/1924 | Runk | 15/210 R |
| 1,682,657 | 8/1928 | Blank | 128/269 |
| 1,853,238 | 4/1932 | Shields | 128/269 |
| 1,857,145 | 5/1932 | Funk | 128/269 |
| 2,847,000 | 8/1958 | Nieburgs | 128/263 |
| 3,203,418 | 8/1965 | Johnston | 128/269 |
| 3,542,025 | 11/1970 | Gustafson | 128/269 |
| 4,140,409 | 2/1979 | DeVries | 128/269 |

FOREIGN PATENT DOCUMENTS

| | | | |
|---|---|---|---|
| 2170 | of 1905 | United Kingdom | 128/269 |
| 460724 | 2/1937 | United Kingdom | 15/210 R |
| 933632 | 8/1963 | United Kingdom | 15/210 R |
| 1478454 | 6/1977 | United Kingdom | 128/269 |

*Primary Examiner*—C. Fred Rosenbaum
*Attorney, Agent, or Firm*—Alan K. Roberts

[57] ABSTRACT

A swab is formed of an elongated support having knit terry pile mounted thereon to form a head. The head is fixed to the support by cementing, staples, binding and/or folding of the support to form a U-shape. The head may also be fastened to the support by quilting. Another method of fastening the head on the support is to fasten a corner of a quadrilateral of knit terry pile to the support at an end of the support, folding the pile to cover the end, and wrapping the thusly folded pile around the support.

5 Claims, 9 Drawing Figures

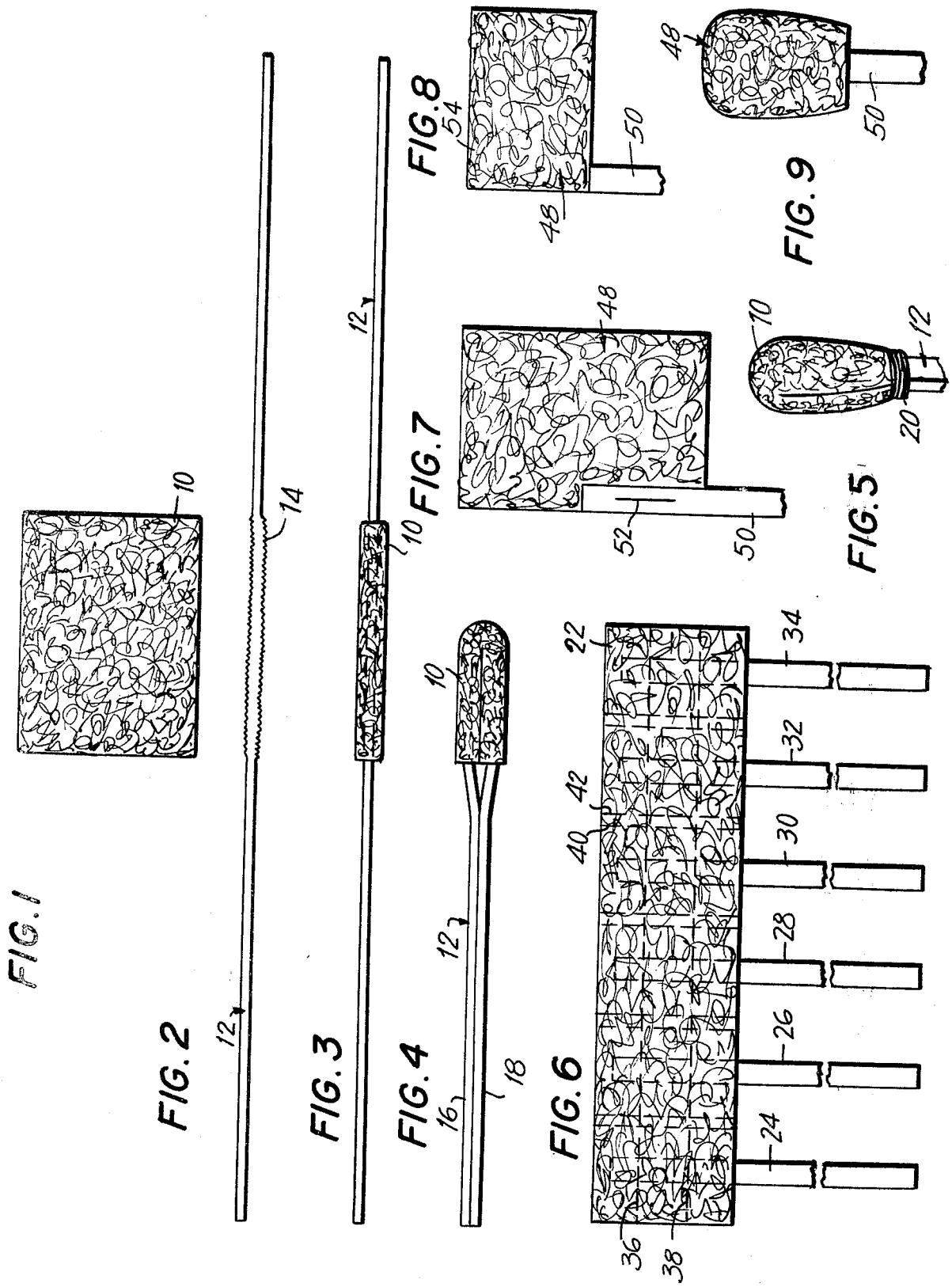

APPLICATOR SWAB AND METHOD OF MAKING THE SAME

FIELD OF THE INVENTION

This invention relates to applicator swabs and to methods of making the same.

BACKGROUND OF THE INVENTION

A wide variety of applicator swabs are known by means of which a substance may be applied to a receiving surface such as the human skin or the like.

One such swab is shown in U.S. Pat. No. 1,332,859 (Hartford Sweet) wherein is shown a sealed cylindrical container having a weakened portion and a hollow wick fitted within the container. A medicament is used to fill the tube and the wick is employed to facilitate the application of the medicament.

In U.S. Pat. No. 1,962,875 (S. M. Reber) there is disclosed a supporting stem having a head arranged at the end thereof with a plurality of absorbent washers being mounted on the stem and a barb being provided on the stem over which the washers pass for holding the washers compressed longitudinally of the stem and against the head.

U.S. Pat. No. 2,490,168 (Oscar Strauss) shows a head arranged on a stem with the head comprising a porous or spongy body such as sponge rubber. The object of this arrangement is to insure the application of medication to remote cavities and passages such as sinuses.

In U.S. Pat. No. 2,579,403 there is shown a swab stick provided with a tip of absorbent gauze material at one end thereof. A blister containing a supply of medicament is embedded in the gauze tip such that slight bending or squeezing of the tip will break the blister and allow its contents to ooze out and soak into the surrounding gauze.

U.S. Pat. No. 3,924,623 (Carl Avery) discloses a swabbing tip for an applicator tube in the form of a cotton-like sheet whose margins are folded inwardly and stuffed into the tube to leave a rounded dome adjacent the end of the tube. The inner face of the sheet is lined with a resilient foam-like layer which enables the size of the dome to be increased while making the dome more quickly saturable.

None of the aforesaid swabs or applicators provide a gentle abrasive action such as is required in many applications while preserving many of the other features desirable in such structures.

SUMMARY OF THE INVENTION

It is an object of the invention to provide an improved swab or applicator which can be gently abrasive.

It is another object of the invention to provide an improved swab, the head of which is less likely to come apart than in constructions heretofore known.

Yet another object of the invention is to provide an improved swab which is washable and reusable and which is for this and other purposes stronger than those heretofore known.

Another object of the invention is to provide an improved swab which is more absorbent than those heretofore known and which is capable of lifting more debris from the surface being treated.

Advantageously, the swabs of the invention are quite useful in a wide variety of applications such as cleaning typewriter keys, cleaning camera lenses, cleaning and restoring oil paintings, applying make-up and removing the same, applying medications, cleaning wounds, removing nail polish, cleaning small and odd shaped places, effecting personal cleanliness, cleaning jewelry and the like, cleaning musical instruments and the like, cleaning grout between bathroom tiles, and so forth.

Moreover, swabs of the invention are useful in cleaning spots from clothing, cleaning wet paint from windows, cleaning leaves on house plants, being used as a substitute for pastry brush, applying shoe polish, applying water repellant silicone to shoes, cleaning louvers and shutters, and so forth.

Swabs of the invention as have been discussed above, are characterized by gentle abrasiveness. They can remove more debris than conventional and previously known swabs because, as will be shown, loops are provided which can hold material and elevate the same away from the site thereof.

The swabs of the invention are provided with soft cushion tips which are softer and thicker than cotton swabs and will hold substantially more moisture. The tips or heads of the swabs of the invention are secure and will not come off. They are, as has been noted above, washable and will come clean in soap and water after many circumstances of use.

Advantageously, the swabs of the invention will not shred or fragment as will cotton swabs. They are advantageously useful in other areas such as, for example, applying butter to corn on the cob or mustard to hot dogs, and so forth.

The swabs of the invention can, moreover, be made in a variety of colors and can be arranged in little holders, for example, of plastic in upright position wherein they will resemble plants or the like with a plastic bubble being fit thereon for purposes of cleanliness.

In accordance with the invention, there is provided more particularly, a swab comprising an elongated support, and a swabbing head on said support, said head being of a terry cloth such as knit terry pile. To fasten the head to the support there may be employed an adhesive. Alternatively, a staple may be employed or, still further, a binding may be employed holding the head on the support.

As an alternative, the support and head may be formed of a U-shape with the head located at the bight of the U. This enables the head to be locked on the support without the possibility of displacement therealong.

The cloth may include a foundation of Jersey with a pile of cotton thereon and may preferably be of a weight of 6.50 ounces per square yard, ±about 20%. The pile may, for example, also be of cotton and polyester blend but, in addition, may be of such other substances as flax or rayon.

According to one method of making a swab in accordance with the invention, the pile may be wrapped around the support and the support folded over to form a U-shape as noted above, with the pile at the bight of the U. The pile may be cemented to the support in this arrangement by way of example. Furthermore, a binding may be wrapped around the pile and support to lock the two together.

According to another method of the invention, there is contemplated stitching the head to the support. Specifically, the pile may be folded to form an elongated U-shaped member and a plurality of supports may be inserted in parallel relationship at spaced stations therein. The pile is then quilted so that the horizontal and vertical stitches quilt the pile to the supports which may thereafter be separated to form separate swabs.

According to yet another method of the invention, it is possible to fasten a corner of a quadrilateral of pile to the support at an end thereof and thereafter fold the pile to cover the end and wrap the thusly folded pile around the support.

Some of the above techniques of the invention may be employed with other than terry cloth material, however, terry cloth material constitutes the preferred embodiment of the invention.

The above and other objects, features and advantages of the invention will be found in the detailed description of preferred embodiments which follow hereinbelow.

BRIEF DESCRIPTION OF DRAWING

In the drawing:

FIG. 1 illustrates a terry cloth quadrilateral prior to application of the same;

FIG. 2 illustrates an elongated support to which the terry cloth of FIG. 1 is to be applied;

FIG. 3 illustrates the application of the terry cloth to the support;

FIG. 4 illustrates deformation of the support and terry cloth to form a swab in accordance with one technique of the invention;

FIG. 5 illustrates a further modification of the swab illustrated in FIG. 4;

FIG. 6 illustrates a quilting technique for fastening terry cloth heads to elongated supports;

FIG. 7 illustrates the beginning of another method of the invention wherein a square of terry cloth is stapled to a support;

FIG. 8 illustates the folding over of the terry cloth of FIG. 7; and

FIG. 9 illustrates the wrapping around of the terry cloth pile completing the method also illustrated in FIGS. 7 and 8.

DETAILED DESCRIPTION

Although the various methods of the invention may be used with a variety of materials to form the tip or head of the swab of the invention, terry cloth, such as knit terry pile constitutes the head in the preferred embodiment of the invention. The characteristics of the terry cloth are preferably as follows:

| Fabric type: | knitted terry pile |
|---|---|
| Basic knit type: | 24 cut Jersey |
| Stitch count: | 24 wales × 22 courses (± 30%) |
| | (wale = No./linear inch vertical) |
| | (course = No./linear inch horizontal) |
| Finished fabric weight: | 6.50 ounces/square yard (±20%) |
| Bursting strength: | 134 pounds (±30%) |
| Fiber content (by weight): | cotton: 66%, polyester: 33% |
| Fiber distribution: | fabric mixture; 100% cotton pile |
| | 100% polyester foundation |
| Yarn details: | pile: 100% cotton; size 30/1 |
| | foundation: 100% polyester |
| | size: 180 denier |
| | type: textured stretch |

The fabric is preferably scoured and bleached. This will greatly increase the fabric's absorbency since polyesters are normally coated with lubricating oils while cotton contains up to 10% by weight of natural waxes. The hand is also improved. Scouring is the more important factor. Bleaching is only necessary when bright colors are desired and/or fast to light pastels.

Finishes are available which will retard or increase this fabric's present absorbency rate. A Mercerized cotton, for example, will have greater total absorbency plus greater strength, easier laundering, and optional luster as compared to the same pre-Mercerized cotton.

Other cellulosic fibers such as flax (linen) and rayons can be substituted for cotton. Flax is costly, difficult to bleach or dye and is less flexible than cotton or rayon. Rayon comes in many types but generally is weaker than cotton especially when wet. HWM or polynosic rayons, however, come close to cotton and offer subtle advantages over cotton in some applications. All rayons absorb more water than cotton, but dry at a slower rate.

The polyester yarn is a type of texturized stretch yarn of which there are many types (Banlon, Helanca, etc). Any thermoplastic filament yarn may be likewise processed such as triacetete or nylon. This yarn type provides a limited reserve stretch and elasticity to that realized through knit construction (rib knit provides more lateral stretch). Most important, however, is the stabilizing effect that polyester has on any fabric. In this respect no other fiber is superior. The use of mixed yarns rather than a blended cotton/poly type accounts for this fabric's high bursting strength, high elasticity, and high pile absorbency.

The support employed in the swab of the invention may also be of a wide variety of types. Thus, for example, the support may be of plastic, wood, cardboard, paper, and so forth. By way of example, the support may be a stick of about 3½ inches in length (folded length) fabricated of plastic and provided with smooth rounded edges and ends.

FIG. 1 illustrates a quadrilateral 10 of terry cloth material such as knit terry pile, the characteristics of which have been mentioned above. This quadrilateral may be a rectangle having for example, the dimensions of 1 inch by 1½ inches.

FIG. 2 illustrates an elongated support 12 having at the center thereof a serration or an application of adhesive indicated generally at 14. This adhesive may be a thermally responsive adhesive or may be, for example, a pressure responsive adhesive. Other types of adhesives are also useful.

FIG. 3 illustrates that the knit terry pile 10 is wrapped around the center of the support 12 and is fastened thereto by means of the aforesaid adhesive.

FIG. 4 illustrates that the elongated support 12 is folded, preferably in half, to form a U-shaped structure having two legs, 16 and 18 juxtaposed in face to face relationship and forming a bight whereat the terry cloth 12 is also formed into a U-shaped structure positioned on the bight and therefore prevented from being displaced longitudinally along the support 12. The legs can be heat sealed or stitched together.

The swab illustrated in FIG. 4 is shown in further modified condition in FIG. 5. Therein is the swab having the terry pile head 10 mounted on the support 12 and having a binding of yarn, generally indicated at 20 wrapped around the head at the base thereof to fasten the head and the support more securely together.

In accordance with a further method of the invention a piece of knit terry pile indicated at 22 is provided in the form of an elongated U-shaped member between the legs of which are inserted a plurality of supports such as those indicated at 24, 26, 28, 30, 32 and 34. These supports are preferably in parallel relationship and are equidistantly spaced while at the same time being inserted between the legs or opposing faces of the terry pile as was noted hereinabove.

In order to lock the supports to the terry pile, there is provided a quilting pattern of stitches such as indicated at 36 and 38 for the horizontal stitches and at 40 and 42 for the vertical stitches. There are two such rows of vertical stitches between adjacent supports and preferably two or more horizontal rows of stitches to lock the various supports to the terry pile.

In the illustration of FIG. 6 it is to be noted that the applicators are cut apart from one another such as by making an incision between vertical seams 40 and 42. On the other hand, it is the horizontal rows of stitches 36 and 38 which penetrate through and make engagement with the supports so that the heads of the applicators are locked to the supports.

FIGS. 7–9 illustrate a further method of the invention. Thus, in FIG. 7 a quadrilateral 48 of terry pile is stapled to a support 50 by means of a staple 52 which may be of metallic type. Thereafter, the terry pile 48 is folded over to form a U-shaped structure having a bight 54 covering the end of the support 52 whereafter, as illustrated in FIG. 9, the flag of terry cloth 48 is wrapped around the support 50 and held thereat either by a binding or by cement.

The use of the terry cloth advantageously provides a gentle abrasiveness which has not been available in swabs heretofore employed. Moreover, the use of terry cloth enables the achieving of the many advantages and objectives which have been stated hereinabove.

The methods of the invention while particularly useful with terry cloth will also find use in connection with other types of materials. Therefore, it is to be considered that the methods of the invention are not strictly limited to the use of terry cloth even though terry cloth constitutes a preferred embodiment of the invention.

There will now be obvious to those skilled in the art many modifications and variations of the structures and methods set forth hereinabove. These modifications and variations will not depart from the scope of the invention if defined by the following claims.

What is claimed is:

1. A swab comprising an elongated support having a length in the order of magnitude of about $3\frac{1}{2}$ inches, and a swabbing head on a portion of said support at one end of the latter, said head being of knit terry pile and including a foundation of cut jersey, said support and head being of U-shape, said U-shape having a bight, said head being located at the bight, said head including opposing sections in face-to-face relationship.

2. A swab comprising an elongated support having a length in the order of magnitude of about $3\frac{1}{2}$ inches, and a swabbing head on a portion of said support at one end of the latter, said head being of terry pile cloth, wherein said cloth includes a foundation of cut jersey and a pile of cotton thereon.

3. A swab comprising an elongated support having a length in the order of magnitude of about $3\frac{1}{2}$ inches, and a swabbing head on a portion of said support at one end of the latter, said head being of terry pile, said pile having a weight of 6.50 ounces/square yard $\pm 20\%$.

4. A method of making a swab comprising mounting terry cloth on an elongated support having a length in the order of magnitude of about $3\frac{1}{2}$ inches, the cloth being fabricated of knit terry pile, the pile being wrapped around the support and the support being folded to form a U-shape with a bight, the pile being located at the bight of the U.

5. A method as claimed in claim 4 wherein the pile is cemented to the support.

* * * * *